United States Patent [19]

Mori et al.

[11] Patent Number: 4,505,893
[45] Date of Patent: Mar. 19, 1985

[54] PURIFIED PLASMINOGEN ACTIVATOR, PROCESS FOR ITS PRODUCTION AND THROMBOLYTIC COMPOSITION CONTAINING IT

[75] Inventors: Toshihito Mori, Tokyo; Hideo Yoshizaki, Saitama; Akio Hasegawa, Shizuoka, all of Japan

[73] Assignees: Asahi Kasei Kogyo Kabushiki Kaisha, Osaka; Kowa Co., Ltd., Aichi, both of Japan

[21] Appl. No.: 519,347

[22] Filed: Aug. 1, 1983

[30] Foreign Application Priority Data

Aug. 2, 1982 [JP] Japan ................ 57/133633

[51] Int. Cl.$^3$ .................... A61K 37/48; C12P 21/00; C12N 5/02
[52] U.S. Cl. ........................ 424/94; 424/95; 424/103; 424/104; 424/105; 424/111; 435/68; 435/241
[58] Field of Search .............. 424/94, 95, 103, 104, 424/105, 111; 435/68, 241

[56] References Cited

PUBLICATIONS

Green Cross Corp.-Chem. Abst., vol. 97, (1982), p. 150, 709e.
Rijken et al.-Chem. Abst., vol. 96, (1982), p. 178 682u.
Collen et al.-Chem. Abst., vol. 96, (1982), p. 149, 150p.
Levin et al., Chem. Abst., vol. 97, (1982), p. 177491q.
McLellan et al.-FEBS Letters, vol. 115, No. 2, (Jun. 1980), pp. 181–184.
Collen et al.-Thromb. Haemostas (Stuttgart), vol. 48, No. 3, (1982), pp. 294–296.

*Primary Examiner*—Sam Rosen
*Attorney, Agent, or Firm*—Sughrue, Mion, Zinn, Macpeak & Seas

[57] ABSTRACT

A plasminogen activator obtained from a tissue cultured liquor of human normal tissue derived cells, e.g., human embryonic derived cells, human placenta derived cells etc., and having the following properties:
(a) molecular weight measured by gel filtration: $63,000 \pm 10,000$,
(b) isoelectric point: 7.0–8.5,
(c) affinity to fibrin: present,
(d) affinity to concanavalin A: present,
(e) optimum pH: 7–9.5, and
(f) stability: does not lose activity at 60° C. for 10 hours but loses about 5% of activity at pH 2–3 at 98° C. for a minute; a process for the production of the aforesaid plasminogen activator; and a thrombolytic composition containing the aforesaid plasminogen activator as an active ingredient are disclosed.

10 Claims, 2 Drawing Figures

PURIFIED PLASMINOGEN ACTIVATOR, PROCESS FOR ITS PRODUCTION AND THROMBOLYTIC COMPOSITION CONTAINING IT

FIELD OF THE INVENTION

This invention relates to a novel purified plasminogen activator, a process for the production thereof and a thrombolytic composition containing it as an active ingredient. More specifically, this invention relates to a plasminogen activator collected from a tissue cultured liquor of human normal tissue derived cells, a process for obtaining the activator in substantially pure form by separation and purification and its use in medicine as a thrombolytic agent, particularly as an active ingredient in a thrombolytic composition.

BACKGROUND OF THE INVENTION

At present, urokinase separated and purified from urine or cultured liquor of kidney cells and streptokinase collected from cultured liquor of Streptococci are plasminogen activators employed in practical use as thrombolytic agents.

However, since urokinase and streptokinase possess poor affinity to fibrin, it is frequently necessary to administer them in large amounts in order to obtain the required effect on treatment. When large doses are administered, side effects such as gastro-internal hemorrhage are manifested. Under such circumstances, a thrombolytic agent having thrombolyzing activity when administered in a small dose and having only a low level of side effects such as causing an gastro-internal hemorrhage has been eagerly sought.

In recent years, a plasminogen activator separated and purified from a tissue cultured liquor of human melanoma cells has been proposed to serve similar purposes (see Japanese Patent Application (OPI) No. 28009/1982). However, since tumor cells are used as a starting material and these are problems with antigenicity and carcinogenicity, such a plasminogen activator cannot be presented for practical use.

The present inventors have discovered, as the result of their study on various tissue cultured liquors of human normal tissue derived cells, that a substance having plasminogen activator activity different from urokinase is contained therein, and they are successfully separated and purified it, thereby having accomplished this invention.

The plasminogen activator of this invention is separated from a tissue cultured liquor of normal tissue derived cells and thus does not have the above-described drawbacks of the plasminogen activator derived from melanoma cells.

SUMMARY OF THE INVENTION

Accordingly, an object of this invention is to provide a novel purified plasminogen activator having high affinity to fibrin and exhibiting a thrombolytic effect when administered in a small dose.

Another object of this invention is to provide a process for the production of said plasminogen activator by separation and purification thereof.

A further object of this invention is to provide a novel thrombolytic composition containing the thus obtained plasminogen activator as an active ingredient and use thereof.

This invention provides (1) a plasminogen activator obtained from a tissue cultured liquor of human normal tissue derived cells and having the following properties:
(a) molecular weight measured by gel filtration: 63,000±10,000,
(b) isoelectric point: 7.0–8.5,
(c) affinity to fibrin: present,
(d) affinity to concanavalin A: present,
(e) optimum pH: 7–9.5, and
(f) stability: does not lose activity held at 60° C. for 10 hours but loses about 5% of activity at pH 2–3 held at 98° C. for a minute. This invention also provides (2) a process for the production of the aforesaid plasminogen activator which is characterized by separating a fraction containing a plasminogen activator from a tissue cultured liquor of human normal tissue derived cells and purifying it; (3) a thrombolytic composition which contains the aforesaid plasminogen activator as an active ingredient and (4) a process for treating a patient requiring thrombolytic activity by administering thereto the plasminogen activator of this invention.

DETAILED DESCRIPTION OF THE INVENTION AND PREFERRED EMBODIMENTS

Figure 2:
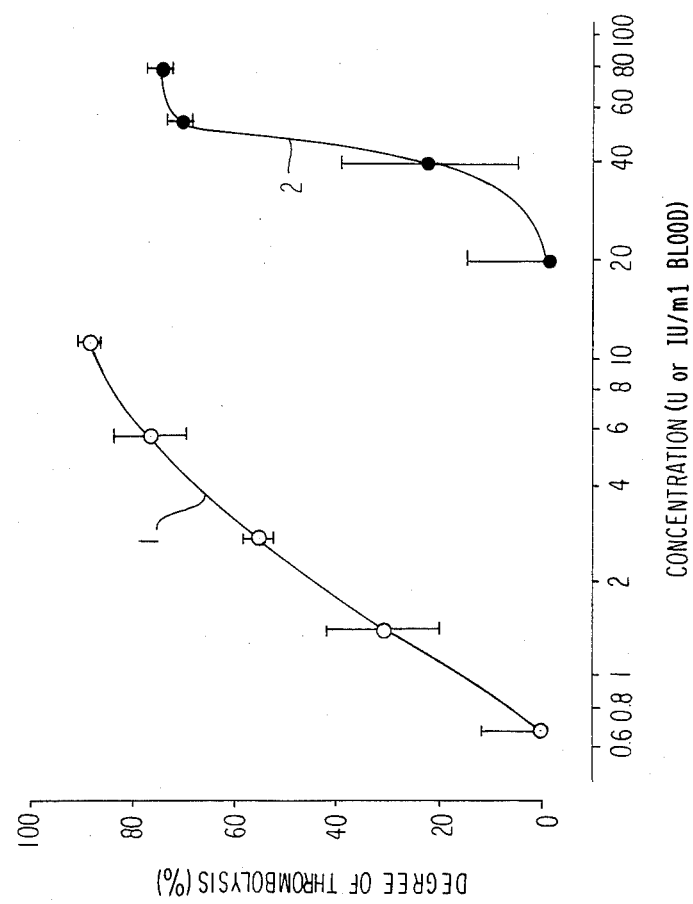

The plasminogen activator of this invention can be produced by separating and purifying it from a tissue cultured liquor using human normal tissue derived cells such as cells derived from human embryonic kidney, intestines, lungs, heart, ureter, skin or foreskin, or the whole embryo, human placenta derived cells or cells derived from human kidney, intestines, lungs, thyroid gland, heart, ureter or skin, in an appropriate growth medium. Of these cells, cells derived from human embryonic kidney, lungs or foreskin are preferably used in this invention.

The tissue cultured liquor of human normal tissue derived cells employed in this invention may be any of those obtained by cultivating cells capable of producing the plasminogen activator in various suitable culture media, and examples thereof include such culture media as those described in Japanese Patent Application (OPI) Nos. 107510/1979, 107511/1979, 19001/1980 and 139323/1980, and Japanese Patent Publication No. 5159/1982.

More specifically, the plasminogen activator of this invention can be produced by contacting the cells which are proliferated in a conventional manner for cultivation of animal cells (e.g., as described in *Tissue Culture Methods and Applications*, edited by P. F. Kruse et al, Academic Press, New York, San Francisco, London (1973)) with a nutrient solution containing carbon sources, nitrogen sources and optionally inorganic salts and/or other additives such as amino acids, vitamins, peptides, hormones, saccharides and organic acids. Usually, the production of the plasminogen activator is performed using at least 0.2 ml of the nutrient solution per 100,000 cells at a temperature of from 25° to 40° C., preferably from 35° to 38° C. During the production, the pH of the nutrient solution is adjusted to 6 to 8, preferably 7.0 to 7.4. The period required for the production is usually 4 to 30 days, but may exceed 30 days. Since the speed of production gradually decreases in the later stage of production, the period which provides the best efficiency is chosen for commercial production. Representative cultivating methods are illustrated in Reference Examples 1 and 2 described hereinbelow.

The overall method for separating and purifying the plasminogen activator from the cultured liquor involves steps conventionally employed in protein chemistry, for example, adsorption using carriers, ion exchange, fractional precipitation, gel filtration, electrophoresis, various types of affinity chromatography, especially those using specific antibodies, etc. There can, for example, be used a fibrin Sepharose column chromatography utilizing a fibrin-bonded agarose, a CM Sepharose column chromatography utilizing a carboxymethyl group-bonded agarose, a ligand-exchange chromatography utilizing a zinc chelate agarose, a lectin column chromatography utilizing a concanavalin A-bonded agarose, an affinity chromatography using antibodies specific to the plasminogen activator of this invention, and a gel filtration method utilizing crosslinked dextran particles. They may be employed either alone or in combination.

One example of a specific overall method for separating and purifying the plasminogen activator involves adding ammonium sulfate to a tissue cultured liquor or a concentrated cultured liquor, separating the formed precipitates, dissolving them in an ammonium thiocyanate solution containing sodium chloride, passing the solution through an anti-urokinase Ig-G Sepharose column and adsorbing the solution onto a fibrin Sepharose column. Thereafter, an eluate obtained by using arginine as an eluent is further passed through an anti-urokinase Ig-G Sepharose column, and freeze dried. The thus obtained powder is dissolved in water and is then gel filtered using Sephadex G-150 (registered trademark by Pharmacia Co.) to obtain the intended plasminogen activator.

There is no doubt that the present substance is a plasminogen activator because it does not dissolve plasminogen-free fibrin, but dissolves plasminogen-containing fibrin.

The physical and chemical properties of the plasminogen activator of this invention thus obtained are described below. The titer measurement was carried out by the following procedures (this also applies to the experiments described hereinbelow).

Using an agar fibrin-added plate prepared by using 95% clotable fibrinogen (plasminogen content: about 50 casein units/g clotable protein) as a starting material, the measurement was carried out by a plate method employing urokinase as the standard. A solution of the substance of this invention was diluted with a 0.067M tris-HCl buffer (pH 8.0) containing 1% gelatin, 0.1M sodium chloride and 0.1% sodium azide, and the concentration of the substance of this invention exhibiting the lyzing zone same as that of 10 IU/ml of urokinase on the fibrin plate was designated as 10 U/ml.

(a) Molecular weight: 63,000±10,000,

This was measured by gel filtration using Sephadex G-150 equilibrated with a 0.01M phosphate buffer (pH 7.0) containing 1.5M sodium chloride, 0.1M EDTA, 0.1M arginine and 0.1% Tween 80 (registered trademark by Kao Atlas). When measured by SDS (sodium dodecyl sulfate) electrophoresis (non-reduction), it was about 70,000.

(b) Isoelectric point: 7.0–8.5,

This was measured by isoelectric point electrophoresis using an ampholyte at about 0° C.

(c) Affinity to fibrin:

20 μl of the substance of this invention (500 U/ml) was added to 950 μl of physiological saline containing 0.2% of plasminogen-free fibrinogen, and then 50 μl of thrombin (30 U/ml) was added thereto. The resulting solution was allowed to stand for 1 hour at room temperature, whereby fibrin was formed. The fibrin was separated, dehydrated and washed with physiological saline. By extracting the substance of this invention from the fibrin with 1 ml of a 2M ammonium thiocyanate solution, it was found that about 70% of the substance was incorporated in the fibrin. For comparison, when urokinase (500 IU/ml) was used, it was not incorporated in the fibrin at all.

(d) Affinity to concanavalin A:

When 2 ml of the substance of this invention (30 U/ml) was dissolved in physiological saline, adsorbed onto a column (0.5×4 cm) of concanavalin A Sepharose (manufactured by Pharmacia Co.), and washed with a 1M sodium chloride solution, nearly 100% of the substance was adsorbed.

Figure 1:
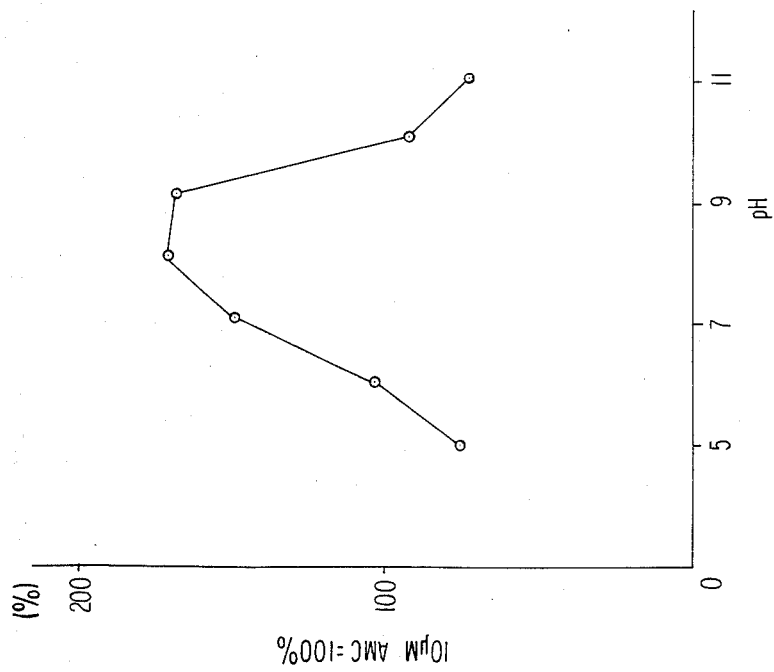
FIG. 1 of the Drawing is a graph showing the optimum pH region for the substance of this invention and, FIG. 2 of the Drawing is a graph plotting the concentration against degree of thrombolysis for urokinase and the plasminogen activator substance of this invention, respectively.

(e) Optimum pH: 7–9.5,

To 50 μl of the substance of this invention dissolved in physiological saline were added 50 μl of plasminogen (8 CU/ml) dissolved in physiological saline containing 10% glycerin and 100 μl of one of a 0.05M citrate buffer (pH 5.0 or 6.0) containing 0.10M sodium chloride, a phosphate buffer (pH 6.0, 7.0 or 8.0) or a glycine-sodium hydroxide buffer (pH 8.0, 9.0, 10.0 or 11.0) (i.e., seven buffers, each at a different pH of 5.0, 6.0, 7.0, 8.0, 9.0, 10.0 or 11.0), and each was preincubated at 37° C. for 30 minutes. Thereafter, 500 μl of Boc-Glu-Lys-Lys-MCA (Peptide Institute, Inc.) dissolved in a 0.15M tris-HCl buffer (pH 8.0) was added, and after incubation at 37° C. for 15 minutes, the reaction was terminated by adding 1 ml of acetic acid, and the formed aminomethylcoumarin was measured by fluorometry to determine the optimum pH. The results of these measurements are shown in FIG. 1.

(f) Stability:

(1) To the substance of this invention dissolved in physiological saline (100 U/ml) was added human serum albumin at a proportion of 1 to 10 mg/ml, and a virulyzing treatment at 60° C. for 10 hours (see Gellis S. S. et al, *J. Clin. Invest.*, 27 239 (1943)) was carried out. A reduction in activity was not observed.

(2) A glycine hydrochloride buffer containing the substance of this invention (100 U/ml) having a pH of 2–3 was prepared, and then a virulyzing treatment at 98° C. for a minute (see Krugman S. et al, *J. Inf. Dis.*, 122 432 (1970)) was carried out, deactivation by about 5% was observed.

(g) Hydrolysis activity on various organic substrates:

To 50 μl of either the substance of this invention (100 U/ml) or urokinase (120 IU/ml) was added 0.1 mM of each of various substrates dissolved in 450 μl of a 0.05M tris-HCl buffer (pH 8.0) containing 0.1M sodium chloride, and each reaction was effected at 37° C. for 15 minutes. The reaction was terminated by adding 0.5 ml of 20% acetic acid, and then measurement for formed aminomethylcoumarin was carried out at an excitation wavelength of 370 nm, a slit width of 5 nm, an emission wavelength of 460 nm and a slit width of 5 nm to determine the hydrolysis activity.

The results are shown in Table 1.

TABLE 1

| | Hydrolysis Activity (%)*1 | |
|---|---|---|
| Substrate*2,3 | Substance of the Invention | Urokinase |
| Pro-Phe-Arg-MCA | 7.81 | 3.89 |
| Z—Phe-Arg-MCA | 4.57 | 2.15 |
| Boc-Glu-Lys-Lys-MCA | 5.16 | 2.82 |
| Boc-Phe-Ser-Arg-MCA | 18.0 | 48.9 |
| Glt-Gly-Arg-MCA | 9.00 | 314 |
| Boc-Ileu-Glu-Gly-Arg-MCA | 17.3 | 3.30 |

[Note]
*1 1 μM Aminomethylcoumarin = 100%
*2 These substrates are described in S. Iwanaga et al, Biochemistry, Pathophysiology, and Clinical Aspects, edited by S. Fujii et al, Plenum Publishing Co., 1979 p. 147.
*3 The -MCA(-methylcoumarineamide) of substrates is released in the form of aminomethylcoumarin upon hydrolysis.

(h) Influence of various proteinase inhibitors:

To 50 μl of either the substance of this invention (100 U/ml) or urokinase (100 IU/ml) were added 50 μl of one of a number of solutions of various proteinase inhibitors and 300 μl of a 0.05M tris-HCl buffer (pH 8.0) containing 0.1M sodium chloride, and each reaction was effected at 37° C. for 5 minutes. Thereafter, 100 μl of either of 0.1 mM of Boc-Phe-Ser-Arg-MCA (Peptide Institute, Inc.) for the substance of this invention or 0.1 mM of Glt-Gly-Arg-MCA (Peptide Institute, Inc.) for the urokinase was added, and each reaction was effected at 37° C. for 60 minutes. Thereafter, 0.5 ml of 20% acetic acid was added to terminate the reaction, which was then measured for the formed aminomethylcoumarin at an excitation wavelength of 370 nm, a slit width of 2 nm, an emission wavelength of 460 nm and a slit width of 2 nm to determine the hydrolysis activity.

The concentrations ($IC_{50}$) of the proteinase inhibitors which inhibit 50% of the activity of the substance of this invention and urokinase were determined and the results are shown in Table 2.

Further, the substance of this invention and urokinase were completely inhibited by diisopropyl fluorophosphate (DFP) which is an inhibitor for serine proteinase.

TABLE 2

| | $IC_{50}$ (M) | |
|---|---|---|
| Inhibitor | Urokinase | Substance of the Invention |
| Aprotinin | >50[1] | >50[1] |
| FOY[2] | 1.46 × 10$^{-7}$ | 1.28 × 10$^{-5}$ |
| Pepstatin | >10$^{-4}$ | >10$^{-4}$ |
| Leupeptin | 8.07 × 10$^{-5}$ | 4.75 × 10$^{-5}$ |
| Chymostatin | >1.60 × 10$^{-4}$ | >1.60 × 10$^{-4}$ |
| DFP (1 × 10$^{-2}$ M) | 100% Inhibited | 100% Inhibited |

[Note]
[1] KIU
[2] Ono Pharmaceutical Co., Ltd.

(i) Enhancement of activity with fibrin:

To 200 μl of a 0.05M tris-HCl buffer (pH 7.5) containing 0.05% of fibrinogen and 0.1M sodium chloride were added subsequently 50 μl of a plasminogen solution (10 CU/ml), 50 μl of either the substance of this invention (5 U/ml) or urokinase (5 IU/ml), 100 μl of a 0.1 mM Boc-Val-Leu-Lys-MCA solution and 100 μl of a thrombin solution (2 U/ml), and the reaction was carried out at 25° C. for 1 hour. The reaction was terminated by adding 500 μl of 20% acetic acid, and then hydrolysis activity was measured in the same manner as in the test (g) above. Further, the same procedure as above was repeated except fibrinogen was not added. The results are shown in Table 3.

TABLE 3

| | Hydrolysis Activity (%)*4 | |
|---|---|---|
| Fibrinogen | Substance of the Invention (5 U/ml) | Urokinase (5 IU/ml) |
| added | 40 | 5.9 |
| not added | 6.3 | 28 |

[Note]
*4 10 μM Aminomethylcoumarin = 100%

As evident from the various properties described above, the plasminogen activator of this invention is a novel purified substance different from urokinase derived from human urine or a tissue cultured liquor of kidney cells.

Thereafter, the thrombolytic activity of the plasminogen activator of this invention was measured by the Chandler's loop method (Quart. J. Exp. Physiol., 46, 1 (1961)). The degree of thrombosis as compared with that of urokinase is shown in FIG. 2. The blood used was human fresh blood, the thrombus forming time was 30 minutes, and the thrombolysis time was 4 hours. In FIG. 2, curve 1 is for the substance of this invention and curve 2 is for urokinase.

As a result, it was confirmed that the thrombolytic activity of the plasminogen activator of this invention was 30 times as strong as that of urokinase. Therefore, the plasminogen activator of this invention is extremely useful as a thrombolytic agent which provides a strong thrombolytic effect upon administration of a small dose.

The substance of this invention is preferably administered intravenously, and the dose, although varying depending on the condition of the patient, may be in the range of 200–1,000,000 units per day. The method for intravenous administration is preferably by injection, or it may be administered by dissolving in a transfusion medium etc.

The substance of this invention can be formulated into e.g., an injectable preparation, for example, by mixing the substance with a conventional excipient for injection, a buffer (e.g., phosphates, sodium chloride, etc.), an isotonic agent, a filler (e.g., mannitol, dextran, cyclodextrin, etc.), a stabilizer (e.g., gelatin, albumin, sulfites, etc.) or the like, dissolving the mixture in distilled water for injection, and freeze-drying and/or vacuum-drying the solution to obtain a drug composition which is filled in a vial for injection.

Other applications of the plasminogen activator, in addition to medical use as a thrombolytic agent, are for preventing the formation of a thrombus by, for example, combining it with materials such as artificial blood vessels, artificial organs etc., or as a diagnostic agent for thrombosis etc.

REFERENCE EXAMPLE 1

Human embryonic kidney cells were implanted in a 100 mm plastic dish at a density of 7×10$^4$ cells/ml, and there was sufficient proliferation by using 10 ml of Medium MEM (minimum essential medium obtained from Eagle) containing 10% fetal calf serum as a growth medium at 37° C. in air containing 5% carbon dioxide. After 5 days, the cells were washed with physiological saline, and the medium was replaced by 20 ml of a serum-free producing medium consisting of Medium 199 (obtained from Morgan) containing 0.5% lactoalbumin hydrolysate and 0.8% fumaric acid. After maintaining the cells in Medium 199 for 7 days, the medium was replaced by a fresh producing medium as described above, and the cultured liquor containing the substance of this invention was recovered.

REFERENCE EXAMPLE 2

Human embryonic lung cells were implanted to a 500 ml spinner flask at a density of $10^5$ cells/ml together with Cytodex I (bead carrier for cell culture, registered trademark by Pharmacia Co.) at a concentration of 2.5 mg/ml, and suspension cultured by using 300 ml of Medium MEM containing 10% fetal calf serum as a growth medium at 37° C. in air containing 5% carbon dioxide, while stirring at a rotation of 60 rpm. After sufficient proliferation of the cells by their cultivation for 8 days, the bead carriers to which the cells had been adhered were washed with physiological saline, and the medium was replaced by 300 ml of serum-free Medium 199 containing 0.5% lactoalbumin hydrolysate and cultivation was continued for 25 days with stirring at a rotation of 60 rpm, while the medium was replaced on every fifth day. Thus the cultured liquor containing the substance of this invention was recovered.

EXAMPLE 1

Ammonium sulfate was added to 4 l of a human embryonic kidney tissue cultured liquor as obtained by Reference Example 1 in a proportion of 300 g/l, and allowed to stand overnight at 4° C. The formed precipitates were collected by filtration, and dissolved in a 1M ammonium thiocyanate solution containing 1M sodium chloride. The obtained solution containing the substance of this invention was 400 ml in liquid volume, and the activity of the solution was 21 U/ml. Further, the specific activity of the solution (activity per unit weight of the proteins (including the substance of this invention) contained therein) was measured according to the method described in White W. F., *Biochemistry*, 5 (1966) wherein concentration of the proteins in the solution was measured from their absorbance at 280 nm. As a result, the specific activity was 10 U/A280. This solution was adsorbed onto a phenyl Sepharose column (1×10 cm) and eluted by a linearly gradient elution method using a 0.01M sodium phosphate buffer (pH 6.8) containing 1M sodium chloride and 1M ammonium thiocyanate at an initial stage while continuously changing the composition of buffer to 0.01M sodium phosphate buffer (pH 6.8) containing 50% of ethylene glycol. The elute was 150 ml in liquid volume, and the activity of the elute was 52 U/ml and its specific activity was 250 U/A 280.

This elute was dialyzed against physiological saline containing 0.1% Tween 80, passed through an anti-urokinase Ig-G Sepharose column and continuously adsorbed onto an arginine Sepharose column (1.5×10 cm). After sufficient washing with a 0.5M sodium chloride solution containing 0.1% Tween 80, a 0.5M arginine solution containing 0.1% Tween 80 was used to elute the substance of this invention. The solution had a liquid volume of 52 ml, and the activity was 98 U/ml and its specific activity was 3200 U/A280.

The above obtained solution was concentrated by freeze drying, and gel filtered through a column (1.5×100 cm) of Sephadex G-150 equilibrated with a 0.01M phosphate buffer (pH 7.0) containing 1.5M sodium chloride, 0.1M arginine, 0.1M EDTA and 0.1% Tween 80, to collect a fraction having activity. The obtained solution containing the substance of this invention was 15 ml in liquid volume, and the activity was 270 U/ml and its specific activity was 12500 U/A280.

EXAMPLE 2

One liter of a human embryonic lung tissue cultured liquor as obtained by Reference Example 2 was passed through an anti-urokinase Ig-G Sepharose column, and then adsorbed onto a fibrin Sepharose column (1.5×10 cm). After washing sufficiently with a 0.5M sodium chloride solution containing 0.1% Tween 80, a 0.5M arginine solution containing 0.1% Tween 80 was used to elute and collect 50 ml of a fraction containing the activity of the substance of this invention. The activity of this solution was 62 U/ml and the specific activity was 950 U/A280. This solution was dialyzed against physiological saline containing 0.1% Tween 80, then adsorbed onto a concanavalin A Sepharose column (1×20 cm), and washed with a 0.01M phosphate buffer (pH 7.0) containing 1M sodium chloride and 0.1% Tween 80, followed by eluting the substance of this invention according to a linearly gradient elution method using the above buffer at an initial stage while continuously changing the composition of buffer to a 0.01M phosphate buffer (pH 7.0) containing 0.4M methylmannoside, 2M ammonium thiocyanate and 0.1% Tween 80. The obtained solution was 25 ml in liquid volume, and the activity was 98 U/ml and its specific activity was 5500 U/A280. After dialysis, the dialysate was concentrated by ultrafiltration and gel filtered by Sephadex G-150 to recover a 15 ml fraction containing activity. The activity was 135 U/ml and the specific activity was 12500 U/A280.

EXAMPLE 3

One liter of each of culture liquors obtained by cultivating cells derived from human embryonic tissues other than the human embryonic kidney and human embryonic lung tissues were purified in the same manner as that described in Example 2, and the results are shown in Table 4.

TABLE 4

|  | Human Embryonic Foreskin | Human Whole Embryo | Human Embryonic Heart | Human Embryonic Intestine |
|---|---|---|---|---|
| After Column Chromatography on Fibrin Sepharose | | | | |
| Liquid Volume (ml) | 45 | 50 | 48 | 48 |
| Activity (U/ml) | 52 | 24 | 75 | 68 |
| Specific Activity (U/A280) | 820 | 450 | 750 | 880 |
| After Column Chromatography on Concanavalin A Sepharose | | | | |
| Liquid Volume (ml) | 24 | 30 | 28 | 26 |
| Activity (U/ml) | 79 | 32 | 105 | 110 |
| Specific Activity (U/A280) | 3500 | 1800 | 3650 | 3900 |
| After Gel Filtration through Sephadex G-150 | | | | |

TABLE 4-continued

|  | Human Embryonic Foreskin | Human Whole Embryo | Human Embryonic Heart | Human Embryonic Intestine |
|---|---|---|---|---|
| Liquid Volume (ml) | 15 | 15 | 15 | 15 |
| Activity (U/ml) | 110 | 55 | 142 | 136 |
| Specific Activity (U/A280) | 11200 | 5600 | 11500 | 12800 |

EXAMPLE 4

The purified substance of this invention was dissolved in physiological saline at the concentration of 1 mg/ml and mixed with Freund's Complete Adjuvant in the mixing ratio of 1/1 by volume. 2 ml of the resulting mixture was subcutaneously injected to a rabbit five times at an interval of one week, and an antiserum specific to the substance of this invention was obtained from the rabbit. The antiserum was purified by a Protein A Sepharose 4B column, and an anti-substance of this invention Ig-G was separated. This Ig-G was combined to CNBr-activated Sepharose 4B in a proportion of 1 mg per ml of gel to prepare Ig-G Sepharose.

Three liters of a human embryonic kidney tissue cultured liquor as obtained by Reference Example 1 was adsorbed onto a column (2×5 cm) of the anti-substance of this invention Ig-G Sepharose, then washed well with physiological saline, and eluted with a 0.2M glycine-hydrochloride buffer (pH 2.5). The pH of the elute was immediately raised to near neutrality, and its activity was measured, whereby a solution having a liquid volume of 200 ml, an activity of 30 U/ml and a specific activity of 500 U/A280 was obtained. This solution was adsorbed to a fibrin Sepharose column (1×5 cm), then washed well with a 0.5M sodium chloride solution, and eluted with 1.5M KSCN. The elute was 20 ml in liquid volume and had an activity of 130 U/ml and a specific activity of 6000 U/A280.

PREPARATION EXAMPLE 1

| Substance of this invention | 24,000 units |
|---|---|
| Purified gelatin | 20 mg |
| Mannitol | 100 mg |
| Sodium chloride | 7.8 mg |
| Sodium phosphate | 15.4 mg |

The above ingredients were dissolved in 2 ml of distilled water for injection, charged into a sterile vial, preliminarily freeze dried at −30° C. to −40° C. for 2 hours, then subjected to primary drying at −30° C. to +20° C. with a degree of vacuum of 0.05-0.1 Torr for 35 hours and to secondary drying at 30° C. with a degree of vacuum of 0.01-0.05 Torr for 5 hours to prepare a vial for injection.

On use, the above is dissolved in 500 ml of physiological saline or glucose solution for injection and instilled intravenously.

PREPARATIVE EXAMPLE 2

| Substance of this invention | 6,000 units |
|---|---|
| Albumin | 5 mg |
| Mannitol | 25 mg |
| Sodium chloride | 1.95 mg |
| Sodium phosphate | 3.85 mg |

The above ingredients were used similarly as in Preparation Example 1 to prepare a vial for injection.

As disclosed hereinbefore, the plasminogen activator of the present invention has a high affinity for fibrin so that the activator preferentially deposits on a thrombus composed of fibrin. Since plasminogen is converted into plasmin (which is capable of dissolving fibrin) on the surface of the thrombus due to the presence of the deposited plasminogen activator of this invention, the plasmin thus formed is less susceptible to being trapped by plasmin inhibitor present in the blood plasma as compared to the case using urokinase. Urokinase, which is not preferentially attracted to fibrin, primarily activates plasminogen present in the blood. The produced plasmin since it is present in blood plasma, is susceptible to being trapped. Accordingly, the plasminogen activator of the present invention can be utilized in relatively low dosages without causing side effects such as gastrointernal hemorrhage.

While the invention has been described in detail and with reference to specific embodiment thereof, it will be apparent to one skilled in the art that various changes and modifications can be made therein without departing from the spirit and scope thereof.

What is claimed is:

1. A purified plasminogen activator obtained from a tissue cultured liquor of human normal tissue derived cells and having the following properties:
   (a) molecular weight measured by gel filtration: 63,000±10,000,
   (b) isoelectric point: 7.0-8.5,
   (c) affinity to fibrin: present,
   (d) affinity to concanavalin A: present,
   (e) optimum pH: 7-9.5, and
   (f) stability: does not lose activity at 60° C. for 10 hours but loses about 5% of activity at pH 2-3 at 98° C. for a minute.

2. A process for the production of a plasminogen activator having the following properties:
   (a) molecular weight measured by gel filtration: 63,000±10,000,
   (b) isoelectric point: 7.0-8.5,
   (c) affinity to fibrin: present,
   (d) affinity to concanavalin A: present,
   (e) optimum pH: 7-9.5, and
   (f) stability: does not lose activity at 60° C. for 10 hours but loses about 5% of activity at pH 2-3 at 98° C. for a minute, which comprises separating a fraction containing the plasminogen activator from a tissue cultured liquor of human normal tissue derived cells and purifying it.

3. A process for the production of a plasminogen activator as claimed in claim 2, wherein the human normal tissue derived cell is selected from cells derived from human embryonic kidney, intestines, lungs, heart, ureter, skin or foreskin, or human whole embryo; human placenta derived cells; or cells derived from human kidney, intestines, lungs, thyroid gland, heart, ureter or skin.

4. A process for the production of a plasminogen activator as claimed in claim 3, wherein the human normal tissue derived cell is selected from cells derived from human embryonic kidney, lungs or foreskin.

5. A process for the production of a plasminogen activator as claimed in claim 2, wherein the tissue cultured liquid is obtained by cultivating the human normal tissue derived cells in at least 0.2 ml of a nutrient solution per 100,000 cells.

6. A process for the production of a plasminogen activator as claimed in claim 5, wherein the cultivating step is performed at a temperature of 25° to 40° C. and a pH of 6 to 8.

7. A process for the production of a plasminogen activator as claimed in claim 6, wherein the cultivation step is performed at a temperature of 35° to 38° C. and a pH of 7.0 to 7.4.

8. A thrombolytic composition which contains an excipient and a plasminogen activator having the following properties:
 (a) molecular weight measured by gel filtration: 63,000±10,000,
 (b) isoelectric point: 7.0-8.5,
 (c) affinity to fibrin: present,
 (d) affinity to concanavalin A: present,
 (e) optimum pH: 7-9.5, and
 (f) stability: does not lose activity at 60° C. for 10 hours but loses about 5% of activity at pH 2-3 at 98° C. for a minute, as a thrombolytic active ingredient.

9. A process for treating a patient requiring thrombolytic activity which comprises administering thereto an effective amount of a plasminogen activator having the following properties:
 (a) molecular weight measured by gel filtration: 63,000±10,000,
 (b) isoelectric point: 7.0-8.5,
 (c) affinity to fibrin: present,
 (d) affinity to concanavalin A: present,
 (e) optimum pH: 7-9.5, and
 (f) stability: does not lose activity at 60° C. for 10 hours but loses about 5% of activity at pH 2-3 at 98° C. for a minute.

10. A process for treating a patient requiring thrombolytic activity as claimed in claim 9, wherein the plasminogen activator is administered in a dose of 200 to 1,000,000 units per day.

* * * * *